United States Patent [19]

Pirson et al.

[11] Patent Number: 5,110,935
[45] Date of Patent: May 5, 1992

[54] COMPOUNDS WHICH ARE ACTIVE AGAINST THE TISSUE FORMS OF MALARIA AND METHOD OF PREPARATION

[75] Inventors: Philippe Pirson, Wezembeek-Oppem; Jean-Bernard Falmagne, Wavre; André Trouet, Winksele-Herent, all of Belgium

[73] Assignee: Ire-Celltarg, S.A., Fleurus, Belgium

[21] Appl. No.: 410,885

[22] Filed: Sep. 22, 1989

[30] Foreign Application Priority Data

Sep. 23, 1988 [FR] France ................. 88 12441

[51] Int. Cl.⁵ .................. A61K 31/47; C07D 215/38; C07D 215/40; C07K 5/02
[52] U.S. Cl. .................. 546/171; 514/314; 514/895; 530/330; 530/331
[58] Field of Search ............ 530/331, 330; 514/19, 514/18, 312, 895, 313, 314; 546/153, 178, 159, 171

[56] References Cited

U.S. PATENT DOCUMENTS 4,703,107 10/1987 Monsyny et al. ............ 530/336
4,897,267 1/1990 Bontemps et al. ............ 424/423

FOREIGN PATENT DOCUMENTS 0286491 10/1988 European Pat. Off. .

OTHER PUBLICATIONS

J. Med. Chem., vol. 31/1988, pp. 870–874, Philip et al.
J. Med. Chem., vol. 29, 1986, pp. 1765–1769, Hofsteenge et al.
Chem. Abst., vol. 99, #17, 1983, p. 637, #140345k, by Hu et al.
J. Med. Chem., vol. 31/1988, pp. 870–874, Philip et al., "Peptide derv. of primaquine . . . ".
Chem. Ab., vol. 99, #17, 1983, p. 637 #140345k, Hu et al., Peptide derv. of Primaquine.
El-Nagyru, CA 102:25012t, Synthesis of dipeptide derv. and studies of antimicrobial activities (1985).

*Primary Examiner*—Jeffrey E. Russel
*Attorney, Agent, or Firm*—Fleit, Jacobson, Cohn, Price, Holman & Stern

[57] ABSTRACT

The invention relates to new quinoline derivatives containing a free amine group and having antimalarial properties, in particular new primaquine derivatives or their addition salts with acids, and to a method for preparing them.

According to the invention, these new derivatives are represented schematically by the formula:

PQ-X in which PQ denotes quinolines containing a free amine group and having antimalarial properties, in particular primaquine; X denotes an amino acid or a peptide of 2 to 4 amino acids; and the PQ-X bond being a covalent peptide bond between the free amine group of PQ and the carboxyl group of X, the PQ-X covalent bond being stable in serum and resistant to lysosomal hydrolases.

In an embodiment of the invention, the amino acid or the first amino acid of a peptide linked to PQ is gamma-L-glutamic acid or beta-aspartic acid linked to PQ via their beta- or gamma-carboxyl group, or L-pyroglutamic acid or aspartic acid linked to PQ via their alpha-carboxyl group.

4 Claims, 1 Drawing Sheet

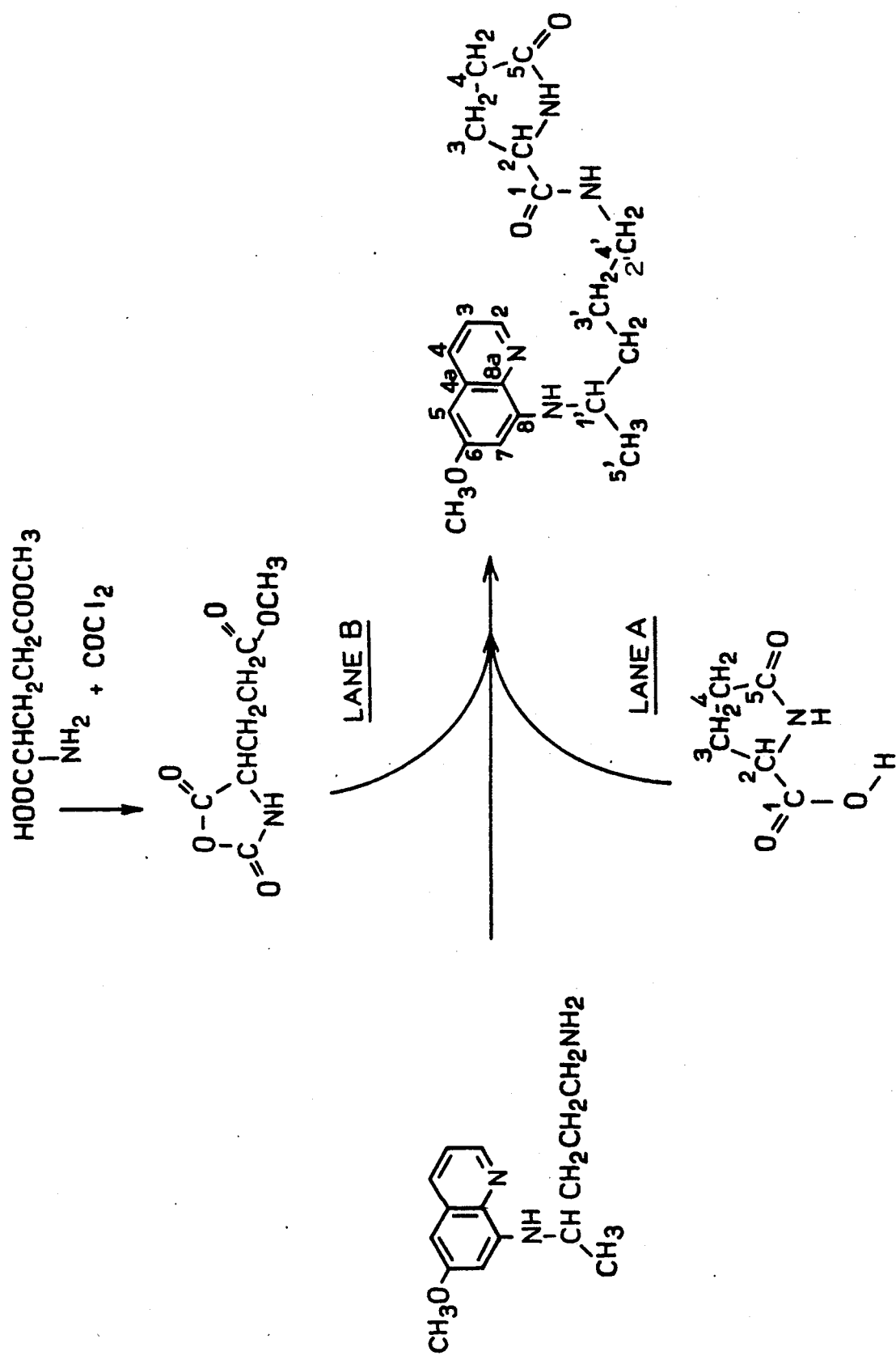

COMPOUNDS WHICH ARE ACTIVE AGAINST THE TISSUE FORMS OF MALARIA AND METHOD OF PREPARATION

The present invention lies within the field of the therapeutic treatment of human malaria, in particular of the tissue forms.

The 2.5 billion people living in endemic areas where malaria is rampant evoke awareness of the failure of the efforts made to date to control this disease. 400 million people live in regions where no prophylactic measure is applied. The World Health Organization (WHO) considers that one million children below the age of five die of the disease each year in the African continent alone.

There are four species of plasmodia responsible for the disease in man. They possess a similar life cycle, involving a vector, a female mosquito of the genus *Anopheles* and a host, man. *Plasmodium falcioarum* (malignant tertian fever) is the most deadly; it is responsible for fatal complications of cerebral malaria and is one of the primary causes of infant mortality in the endemic regions.

*Plasmodium vivax* and *P. ovale* (benign tertian fever) are less virulent, but produce latent forms in the hepatocytes, hypnozoites. These are the forms responsible for the classical relapses which can persist for long periods (two to five years) after a single infection. *P. malariae* is less widespread; it is responsible for chronic renal diseases such as nephritis and fatal nephrotic syndromes, and can persist in the blood for several years.

More specifically, the present invention relates to the development of new drugs which are active against human malaria, in particular its tissue forms, namely new aminoquinoline derivatives and in particular new primaquine derivatives whose structure is as follows:

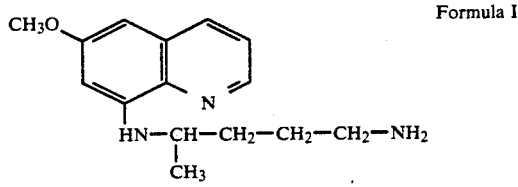

Formula I

In the present patent application, aminoquinoline is understood to mean a quinoline derivative possessing at least one free amine group, especially 8-aminoquinolines including primaquine [6-methoxy-8-(4-amino-1-butylamino)quinoline], and also other 8-aminoquinolines having a primary amine group at the end of a side chain, such as quinocide [6-methoxy-8-(4-aminopentylamino)quinoline] or SN 3883[6-methoxy-8-(4-aminobutylamino)quinoline].

However, there also exist other primaquine derivatives, in which the modifications affect the quinoline ring-system (at the 2-, 4-, 2,4-, 5- and 4,5-positions) and the (4-amino-1-alkylbutylamino) side chain, the present invention relating to such derivatives.

In the classical treatments of malaria, tissue schizonticides, essentially represented by the 8-amino-quinolines (primaquine, quinocide), are responsible for causal prophylaxis, namely the prevention of blood infection by destruction of the primary (exoerythrocytic) tissue forms of *P. falciparum*, and for radical treatment by elimination of the secondary tissue forms of *P. vivax* and *P. ovale*. Primaquine, a 6-methoxy-8-(4-amino-1-methylbutylamino)quinoline of formula I, introduced more than thirty years ago, is clinically effective on the persistent tissue forms of *P. vivax* and *P. ovale* in man and is still a drug of choice.

Nevertheless, the toxicity of primaquine limits its use to a controlled clinical application. The most serious toxic effect is hemolysis, especially for individuals possessing ar erythrocytic genetic deficiency, for example of glucose-6-phosphate dehydrogenase. Methemoglobinuria and gastrointestinal disorders as well as certain effects on the central nervous system are also some significant toxic effects of primaquine and other 8-aminoquinolines.

The number cf antimalarial drugs possessing causal prophylactic or radical curative therapeutic activity is extremely limited Primaquine is the only drug for radical curative treatment, but the toxic side effects severely limit its therapeutic use.

It should be noted that only compounds belonging to the 8-aminoquinoline families are likely to produce a radical cure.

The object of the present invention is hence to propose new antimalarial quinoline derivatives, in particular new 8-aminoquinoline derivatives possessing an improved therapeutic index.

In other words, the object of the present invention is to reduce the intrinsic toxicity of said antimalarial quinolines such as primaquine, and to enhance their activity, in particular as regards primaquine, against the hepatic tissue forms.

It will be noted that L-leucine linked to primaquine was proposed in Application EP 37,388, on account of its importance as a linker or arm and hence in the context of a carrier-arm-drug conjugate. In point of fact, L-leucylprimaquine regenerates the free active principle when subjected to lysosomal digestion. However, the therapeutic index of derivatives of PQ with unconjugated adjacent L-leucine proves less advantageous than those of the derivatives which form the subject of the present invention.

The subject of the present invention is, in effect, new antimalarial aminoquinoline derivatives, in particular new primaquine derivatives, the essential feature of which is that they are represented schematically by the formula PQ-X, in which:

PQ denotes an antimalarial aminoquinoline, in particular primaquine, and

X denotes an amino acid or a peptide of 2 to 4 amino acids, the amino acid or acids being chosen from natural amino acids and their derivatives, the amino acid adjacent to PQ being chosen from alpha- or beta -aspartic acid, gamma-glutamic acid or pyroglutamic acid, the PQ-X bond being a covalent peptide bond between the free amine group of PQ and a carboxyl group of the amino acid or of the first amino acid of X.

In the present application, "alpha- (or beta) aspartic (or gamma glutamic) acid" is understood to mean that the adjacent amino acid is linked to PQ under the form of an ester via its alpha- or beta- (or gamma , respectively) carboxyl group.

Primaquine acts as an oxidizing agent and destabilizes the red cell membrane, inducing a hemolysis which is the source of its main toxicity.

The addition of an amino acid or a peptide, according to the present invention, reduces the penetration of primaquine into the red cells as a result of stearic hindrance.

In addition, the activity of these new derivatives was found to be much greater. A significant drop in toxicity was also observed.

According to another subject of the present invention, it was discovered that this objective was also achieved if, generally speaking and preferably, X is chosen in such a way that the covalent bond between PQ and X is stable in serum and resistant to lysosomal hydrolases. The benefit of the amino acid or peptide is then more fully in evidence. This further condition is fulfilled, in particular, when X is gamma-aspartic or gamma-glutamic acid or pyroglutamic acid.

Thus, advantageously according to the invention, the amino acid or the first amino acid of the peptide is gamma-glutamic or beta-aspartic acid linked to PQ via its gamma- or beta-carboxyl group, or alternatively pyroglutamic or aspartic acid linked to PQ via its alpha-carboxyl group.

According to the present invention, the amino acid adjacent to PQ is chosen from within the D or L series, but preferably from within the L series.

In a preferred embodiment, the subject of the present invention is new primaquine derivatives, the essential feature of which is that they are represented schematically by the formula PQ-X, in which:

PQ denotes an antimalarial aminoquinoline, in particular primaquine; and

X denotes an amino acid, gamma-L-glutamic acid, L-pyroglutamic acid, alpha-L-aspartic acid or beta-L-aspartic acid;

the PQ-X bond being a covalent peptide bond between the free amino group of primaquine and the carboxyl group of X, stable in serum and resistant to lysosomal hydrolases.

The derivatives in question are hence N-($\alpha$-L-pyroglutamyl)-PQ, N-($\gamma$-L-glutamyl)-PQ, N-($\alpha$-L-aspartyl)-PQ and N-($\beta$-L-aspartyl)-PQ.

It should be clearly understood that the parent product aminoquinoline (PQ) can also be substituted without departing from the scope of the present invention, provided it comprises an aminated side chain onto which can be grafted one or more amino acids (X) according to the present invention.

The parent products PQ, as well as the products PQ-X obtained, can take the form of their addition salts with acids.

The subject of the present invention is also a method for preparing these new antimalarial aminoquinoline derivatives, in particular primaquine derivatives.

In the essential feature of the method according to the present invention, an amino acid or peptide in acid form, in which one amine groups and, where appropriate, the $\alpha$-$\beta$- or $\gamma$-carboxyl group are optionally protected, is reacted with the aminoquinoline or one of its salts, hence bearing a free amine group, in the presence of a condensing agent.

The groups protecting the amino groups are conventional groups, but tert-butyloxycarbonyl or benzyloxycarbonyl is preferably used.

The groups protecting the carboxyl group are conventional groups such as tert-butyl or benzyl.

The acid group of the amino acid or peptide can also be activated, for example in the form of an ester with N-hydroxysuccinimide.

In general, the condensing agent is a carbodiimide such as dicyclohexylcarbodiimide.

According to a particular embodiment of the method, the starting materials are an aminoquinoline salt, for example diphosphate, and the amino acid or peptide in the amino group and, where appropriate, the $\alpha$-$\beta$- or $\gamma$-carboxyl group are optionally protected, for example by a tert-butyloxycarbonyl or benzyloxycarbonyl group for the amino group and a tertbutyl or benzyl group for the carboxyl group, and the following steps are performed:

a) N-hydroxysuccinimide, or any other group activating the unprotected acid group of the amino acid or peptide, is reacted with the optionally protected derivative of the amino acid or peptide, b) the aminoquinoline such as primaquine, liberated from its salt, for example with ammonia solution, is reacted; it is hence reacted with, for example, the N-hydroxy-succinimide ester of the protected derivative of the amino acid or peptide, c) the crude product thereby obtained is purified by chromatography on silica gel, and d) the protective groups, where appropriate, are then cleaved off in the presence of acid, for example trifluoroacetic acid, to give the derivative PQ-X in the form of a salt, for example trifluoroacetate, or are cleaved off by hydrogenolysis.

This group can, in effect, be removed under conditions which do not destroy the peptide bond formed.

According to another special feature of the method, the trifluoroacetate counter-anion is exchanged for hydrochloride or phosphate.

With the object of inhibiting oxidation reactions, another special feature of the method provides for treatment of the aqueous solution containing the hydrochloride salt of derivatives according to the present invention with sodium bisulfite.

A derivative PQ-X in which X denotes L-pyroglutamic acid can be prepared by converting an ester at the $\gamma$-position of L-glutamic acid to an N-carboxy anhydride, the reaction being performed in the presence of phosgene, which N-carboxy anhydride derivative is coupled to PQ by reaction at 0° C. in THF to give the derivative (L-pyroglutamyl)-PQ.

Advantageously, the L-glutamic acid ester is gamma-methyl glutamate or gamma-benzyl glutamate.

The subject of the present invention is also pharmaceutical compositions containing, by way of active principle, the new derivatives according to the present invention or their pharmaceutically acceptable salts.

Other features and advantages of the invention will become apparent in the light of the examples which follow, produced with reference to FIG. 1, which shows two methods of synthesis of the derivative N-($\alpha$-L-pyroglutamyl)-primaquine.

BRIEF DESCRIPTION OF THE DRAWING

The figure illustrates two methods of synthesis of the derivative N-($\alpha$-L-pyroglutamyl)-primaquine.

DETAILED DESCRIPTION OF THE INVENTION

EXAMPLE 1

SYNTHESIS OF L-$_{65}$-GLUTAMYL OR L-PYROGLUTAMYL DERIVATIVES OF PRIMAQUINE

1. Synthesis of N-($\alpha$-L-pyroglutamyl)primaquine (pGLU-PO)

The pyroglutamic acid derivative of primaquine (PQ) is obtained according to two methods, A and B, by the condensation of PQ either with pyroglutamic acid (method A) or with an activated ester of glutamic acid (method B). The two methods of synthesis are shown schematically in FIG. 1. This compound is obtained in the form of a base (M.W. 370.43), of a monohydrochloride salt (M.W. 406.89) and of a monophosphate salt (M.W. 468.44).

1.1. Synthesis according to method A

The pyroglutamic acid derivative of PQ is obtained in two stages from PQ diphosphate and pyroglutamic acid.

a) Primaquine base

PQ in its free form is obtained from PQ diphosphate by neutralizing an aqueous solution containing the PQ salt with 25% strength NH OH until a pH of 8 is obtained, followed by vigorous extraction of the PQ base with $CH_2Cl_2$.

b) Activation of pyroglutamic acid

The N-hydroxysuccinimide ester of L-pyroglutamic acid is obtained by the reaction of pyroglutamic acid, dissolved in dimethylformamide or DMF (1 g in 5 ml), with one equivalent of N-hydroxysuccinimide (891 mg) and one equivalent of a dicyclohexylcarbodiimide (1.6 g). The mixture is stirred at 4° C. for 16 hours.

c) L-Pyroglutamylprimaquine

The primaquine base is dissolved in a minimum amount of $CH_2Cl_2$ and added to the activated ester at 4° C. The reaction mixture is stirred at 4° C. for 16 hours. The dicyclohexylurea is filtered and the solvents are evaporated off.

The crude reaction product is then taken up in $CH_2Cl_2$ and is washed three times with 5% strength $NaHCO_3$ solution and thereafter three times with saturated NaCl solution. The dichloromethane phase is dried over $Na_2SO_4$, filtered and evaporated to dryness. The product is eluted with a 95:5 dichloromethane/methanol mixture. The pure fractions are combined and the solvents are evaporated off. 1.36 g of L-pyroglutamylprimaquine are thus isolated (47.5% yield).

1.2. Synthesis according to method B a) Primaquine base

PQ in its free form is obtained from PQ diphosphate by neutralizing an aqueous solution containing the PQ salt (9.1 g in 100 ml) with the equivalent amount of 1 molar NaOH (20 ml). The pH of the final solution is between 9.5 and 10. The PQ base is then extracted with $CH_2Cl_2$ (3×100 ml). The organic phases are combined, and dried by entrainment with toluene or tetrahydrofuran (THF).

b) Derivatization to an N-carboxy anhydride (NCA)

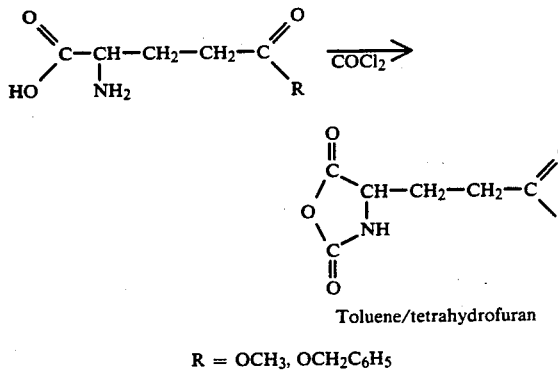

Toluene/tetrahydrofuran

R = $OCH_3$, $OCH_2C_6H_5$

Derivatization of the amino acid to an N-carboxy anhydride is accomplished by reaction of the amino acid with phosgene. More precisely, 10 g of gamma-methyl glutamate are suspended in 20 ml of dry THF (refluxing over sodium in the presence of benzophenone).

Separately, a solution of phosgene in THF is prepared from gaseous phosgene condensed at low temperature and THF.

The phosgene solution (40 ml; 2.75 M) is then added to the suspension of the amino acid in THF via a capillary and with an excess pressure of nitrogen.

The apparatus is then equipped with a dry-ice condenser, which is itself connected to two empty traps in series followed by a tube dipping into concentrated NaOH solution (trapping of the excess phosgene). The reaction mixture is brought to the refluxing temperature. This temperature is maintained until the amino acid has dissolved completely equivalent to 2 and a half hours. The solvents are evaporated to dryness under vacuum and with protection from atmospheric moisture. The N-carboxy anhydride is obtained in the form of a white powder. The NCA is crystallized, if desired, by dissolution in hot (dry) ethyl acetate, addition of an equal volume of (dry) petroleum ether and cooling.

c) Coupling reaction

The NCA derivative, dissolved in (dry) tetrahydrofuran THF, is diffused slowly (3 hours) into a solution of primaquine base in THF in the dry state at 0° C. $CO_2$ is evolved from the reaction mixture, indicating opening of the NCA ring. The $CO_2$ is assayed by the formation of $BaCO_3$ on passage of the evolved gas into barium hydroxide solution.

After reaction, the solvent is evaporated off to dryness and the crude reaction product is purified by chromatography on $SiO_2$ ($CH_2Cl_2$/MeOH).

1.3 Salt formation

1) Hydrochloride salt pGLU-PQ is dissolved in water in the presence of two equivalents of hydrochloric acid and lyophilized. The operation is repeated again.

2) Phosphate salt pGLU-PQ is dissolved in isopropanol and added to one equivalent of phosphoric acid dissolved in isopropanol (1.5% weight/volume). The salt does not precipitate under these conditions. The solvent is evaporated off and the salt is taken up in water and lyophilized.

1.4. Physical and chemical properties:

1.4.1. L-Pyroglutamyl-PQ

| Purity by TLC | |
|---|---|
| System: | $CH_2Cl_2$/MeOH (10:1 by volume) |
| Plates: | Si-60 |
| Rf: | 0.26 |
| Purity by TLC: a single spot | |
| Purity by HPLC | |
| Column: | $C_8$ grafted silica (Waters). |
| Eluent: | 0.1M ammonium formate pH 3.85/acetonitrile mixture (70:30 by volume). |
| Detector: | UV at 363 nm |
| Flow rate: | 2 ml/min |
| $t_R$: | 4.8 min |
| Purity by HPLC: usually >99% at the surface; solution 1 mg/ml in 0.1M ammonium formate buffer pH 3.85. | |
| Melting point: N.D. | |
| Optical rotation: N.D. | |
| Stability: | pGLU-PQ is: unstable at room temp. and in the air; stable at room temp. under inert atmosphere (argon). |
| Nuclear magnetic resonance: | |
| $^1$H NMR: | ($CDCl_3$ - TMS) |

-continued

| | |
|---|---|
| $^{13}$C NMR: | (CDCl$_3$ - the middle line of the CDCl$_3$ serving as a reference at 77.00 ppm). |

179.198 (c-5 pGLU); 172.233 (c-1 pGLU); 159.152 (c-6 PQ); 144.640 (c-8 PQ); 144.106 (c-2 PQ); 135.022 (c-8a PQ); 134.696 (c-4 PQ); 129.704 (c-4a PQ); 121.709 (c-3 PQ); 96.647 (c-7 PQ); 91.507 (c-5 PQ); 56.985 (c-2 pGLU); 54.978 (6-OCH$_3$ PQ); 47.589 (c-1' PQ); 39.248 (c-4' PQ); 33.539 (c-2' PQ); 29.147 (c-4 pGLU); 25.523 (c-3 pGLU); 20.246 (c-5 PQ).

Infrared:

| cm$^{-1}$ | (%) |
|---|---|
| 3386 | (49%) broad; |
| 1684 | (45%) broad; |
| 1521 | (45%); |
| 1457 | (51%); |
| 1387 | (49%); |
| 1220 | (54%); |
| 1158 | (53%); |
| 822 | (56%); |
| 792 | (56%)' |
| 668 | (52%). |

Mass:

FAB +: 371.2 (M + 1)$^+$
175.1 (C$_{10}$H$_{10}$N$_2$O)$^+$
FAB −: 369.1 (M − 1)$^+$

2. Synthesis of N-(γ-L-glutamyl)primaquine (gGLUC-PQ)

The γ-glutamic acid derivative of primaquine is obtained according to the method of synthesis described below, in the form of a dihydrochloride salt (M.W. 388.45 +72.92=461.38) and of a monophosphate salt (M.W.: 468.44).

2.1. Synthesis

The glutamic acid derivative of PQ is obtained in two stages from PQ diphosphate and from L-glutamic acid in which the amino group is protected either by a tert-butyloxycarbonyl group (N$^α$-t-BOC) or by a benzyloxycarbonyl group (N$^α$-CBZ). The α-carboxyl group is protected either by a t-butyl group or by a benzyl group.

a) Primaquine base

Primaquine in its free form is obtained from PQ diphosphate by neutralizing an aqueous solution containing the PQ salt with 25% strength NH$_4$OH until a pH of 8 is obtained, followed by vigorous extraction of the PQ base with CH$_2$Cl$_2$.

b) Activation of the protected amino acid

The N-hydroxysuccinimide ester of the protected glutamic acid is obtained by the reaction of 5.9 mmol of N$^α$-t-BOC-L-GLU-α-t-butyl (1.8 g) - or of N$^α$-CBZ-L-GLU-α-O-benzyl - with 5.9 mmol of N-OH-succinimide (0.68 g) and 5.9 mmol of dicyclohexylcarbodiimide (1.21 g) dissolved at 0° C. in ethyl acetate.

c) (N$^α$-t-BOC-L-Glutamyl)-PQ

After 16 hours, reaction between the protected glutamic acid and NHS at 0° C., 5.9 mmol (1.53 g) of PQ base are added. After 17 hours, the dicyclohexylurea is filtered off and the solvent is driven off under vacuum.

The brown oil obtained is dissolved in CH$_2$Cl$_2$ and washed with water. The organic phase is dried over sodium sulfate, filtered and evaporated. The product is purified on silica gel, using a dichloromethane/methanol mixture as eluent. The pure fractions are combined, and the evaporated eluent fields a more or less crystalline product.

Yield: 65%.

d) Deprotection

1) Deprotection with trifluoroacetic acid and formation of the hydrochloride salt. The compound obtained above is dissolved in 45 ml of a 1:1 mixture of dichloromethane and trifluoroacetic acid. The mixture is stirred for 4 hours at room temperature. The solvents are evaporated off under vacuum and the residue is taken up in water and washed several times with an ethyl acetate/ether mixture (50:50 by volume). The aqueous phase is recovered and lyophilized. The orange-yellow powder is taken up in water and two equivalents of 0.5 N hydrochloric acid are added. The solution thereby obtained is then lyophilized. The cycle is repeated twice. The hydrochloride salt is isolated and kept under argon.

2) Deprotection by hydrogenolysis and formation of the phosphate salt. (N$^α$-CBZT-α-O-benzyl-L-glutamyl)primaquine, obtained above, is dissolved in ethyl acetate (100 ml per 0.01 mol). The solution is completed with absolute ethanol (150 ml). The one-liter round-bottomed flask is then purged with argon. Hydrogen is introduced after the flask has been evacuated. The vacuum/hydrogen cycle is repeated twice. The hydrogen pressure is brought to 20 Psi. After 2 and 4 hours, reaction, the flask is evacuated and then filled with hydrogen to a pressure of 20 Psi. After 6 or 7 hours' reaction, the hydrogen is driven off under vacuum and the solvents are evaporated off. The gamma-glutamyl primaquine is dried under vacuum for 16 hours.

Yield: 100%.

Formation of the phosphate salt (γ-L-Glutamyl)primaquine (0.01 mol) is dissolved in 60 ml of ethanol and 10 ml of ethyl acetate. This mixture is added to a solution of phosphoric acid (Merck 573; analytical grade: 85% in isopropanol). The volume is brought to 250 ml and the precipitate is stirred for 1 hour. The precipitate is filtered off on a Millipore FH membrane under argon. The product is rinsed twice with isopropanol, transferred to a round-bottomed flask and dried under vacuum for ~20 hours. 4.4 g of (γ-L-glutamyl)primaquine phosphate are thereby isolated (90%).

2.2 Physical and chemical properties 2.2.1. (Gamma-L-glutamyl)primaquine

| | |
|---|---|
| Purity by TLC | |
| System: | CH$_2$Cl$_2$/MeOH (18:2 by volume). |
| Plates: | Si-60 |
| Rf: | 0.15 |
| Purity by TLC: a single spot | |
| Purity by HPLC | |
| Column: | C$_8$ grafted silica |
| Eluent: | 0.1M ammonium formate pH 3.85/acetonitrile mixture (70:30 by volume). |
| Detector: | UV at 363 nm |
| Flow rate: | 2 ml/min |
| t$_R$: | 2.2 min |
| Purity HPLC: usually >99% | |
| Melting point: N.D. | |
| Optical rotation: N.D. | |
| Stability: | gGLU-PQ is: unstable at room temp. and in the air; stable at room temp. under inert atmosphere (argon) |
| Nuclear magnetic resonance: | |
| $^1$H NMR: | (CDCl$_3$ - TMS) N.D. |
| $^{13}$C NMR: | (CDCl$_3$ - the middle line of the CDCl$_3$ serving as a reference at 77.00 ppm). |
| Infrared: | |
| Mass | |

-continued

| | |
|---|---|
| 2.2.2 | (Gamma-L-glutamyl)primaquine hydrochloride<br>Purity by HPLC:<br>Usually >99%<br>Conditions identical to those of 4.2.2.1. |
| 2.2.3. | (Gamma-L-glutamyl)primaquine phosphate<br>Purity by HPLC:<br>Usually >99%<br>Conditions identical to those of 4.2.2.1. |

EXAMPLE 2: IN VITRO EXPERIMENTAL STUDY

1. Stability in the presence of serum 1.1 Protocol

The influence of serum on the stability of primaquine (PQ) and its derivatives is determined by incubating these compounds at 37° C. at a concentration of 100 μg/ml in 95% fetal calf serum (FCS, Flow Laboratories) or human serum and phosphate-buffered saline (0.15 M PBSA, pH 7.2) as a control. All the solutions are sterilized by filtration on a Millipore filter (Millex GV) of porosity 0.20 μm.

At interval of time, 1-ml samples are withdrawn and the serum proteins are then extracted from them by precipitation with acetonitrile. For this purpose, an identical volume of acetonitrile is added to each sample. After vigorous mixing in a Vortex mixer, the samples are left for 1 hour at 4° C. and protected from light and then centrifuged for 5 minutes at 12,000 g. The supernatants are collected and then analyzed by HPLC (20- to 50-μl aliquot) under the standard conditions.

1.2. Results

The results for the stability of primaquine and its two derivatives in the presence of fetal calf serum are recorded in Table 1; the results are expressed as a % of the initial concentration (time 0) after extraction.

In the presence of serum, primaquine is unstable; it is gradually degraded and reaches 7% after 24 hours. Under the experimental conditions used, a second peak (Y) is observed in HPLC ($t_R$: 4.2 minutes) after 2 hours' incubation, never, however, exceeding 10%.

gGLU-PQ is for at least 3 hours, then a gradual decrease in the relative concentration is observed after 6 hours' incubation, without a significant increase in the PQ concentration. pGLU undergoes no modification during its incubation in serum. Neither derivative regenerates primaquine in the presence of serum after 24 hours' or 48 hours' incubation.

Similar results are obtained on incubation of the compounds in the presence of human serum. In a buffered solution (PBS), the compounds are stable, with no significant spectral modification after 24 hours.

The results obtained show that the covalent bond between the amino acid and primaquine is stable and resistant to serum enzymes.

2. Hydrolysis in the presence of lysosomal enzymes 2.1. Protocol

The compounds, at a final concentration of 15 μg/ml, are incubated in 50 mM acetate buffer, pH 4.5, at 37° C. in the presence of 5 mM cysteine and a lysosomal enzyme fraction (0.15 mg protein/ml) purified from rat liver.

The purified lysosomal fraction is prepared according to the method described by Trouet (1974, Meth. Enzymol., 31, 323–334).

At intervals of time, corresponding samples are taken from the incubation. The enzyme reaction is stopped by adding 10 μl of 10M HCl per ml of sample. A volume of 20 μl is withdrawn and analyzed directly by HPLC under the standard conditions.

2.2. Results

The effect of lysosomal hydrolases at pH 4.5 on PQ and its derivatives is shown in Table 2 below.

TABLE 2

Lysosomal hydrolysis of primaquine and its amino acid derivatives.

| COMPOUND [a] | | INCUBATION TIME (hours) [b] | | | | | |
|---|---|---|---|---|---|---|---|
| | | 0 | 1 | 2 | 3 | 6 | 24 | 48 |
| Primaquine | | 100 | 94 | 96 | 84 | 87 | 68 | — |
| gGLU-PQ | PQX | 100 | 104 | 95 | 98 | 101 | 105 | — |
| | PQ | 0 | 0 | 0 | 0 | 0 | 0 | — |
| pGLU-PQ | PQX | 99 | 94 | 97 | 97 | 96 | 76 | 47 |
| | PQ | 1 | 0 | 0 | 0 | 0 | 0 | 0 |

[a]: The compounds are incubated at pH 4.5 in the presence of lysosomal enzymes (0.15 mg protein/ml) and 5 mM cysteine, and then analyzed by spectrophotometry after HPLC. The initial purity of the compounds, determined by HPLC, is 99.5%, 99.7% and 98.8%, respectively.
[b]: The results represent the relative concentration of primaquine (PQ) and derivatives (PQX) in terms of the incubation time, expressed as a percentage of the initial concentration (time 0) after extraction.

In the presence of lysosomal enzymes, neither derivative of primaquine regenerates the parent primaquine after 24 or 48 hours' incubation.

The covalent bond between the amino acid and the PQ side chain is resistant to lysosomal hydrolysis. A gradual decrease in the relative concentration of PQ, reaching 68% after 24 hours, is, however, observed without the appearance of a new peak in HPLC. The same phenomenon is also observed in the case of pGLU-PQ, appearing only after 6 hours' incubation 3. Permeability of human erythrocytes to primaquine and derivatives 3.1. Protocol Fresh human blood (A+) on CPDA is washed twice in RPMI medium containing 20 mM glucose at pH 7.4, and then resuspended in the same medium at 37° C. to

TABLE 1

Stability of primaquine and its amino acid derivatives in the presence of fetal calf serum

| COMPOUND [a] | | INCUBATION TIME (hours) [b] | | | | | |
|---|---|---|---|---|---|---|---|
| | | 0 | 1 | 2 | 3 | 6 | 24 | 48 |
| Primaquine | PQ | 100 (2) | 98 (12) | 87 (9) | 77 (6) | 34 (4) | 2 | — |
| | Y | 0 | 0 | 5 | 10 | 11 | 5 | — |
| gGLU-PQ | PQX | 98 (1) | 96 (3) | 95 (8) | 94 (6) | 83 (3) | 51 (4) | — |
| | PQ | 2 (1) | 3 (0) | 4 (2) | 4 (2) | 4 (1) | 4 (3) | — |
| pGLU-PQ | PQX | 100 (0) | 100 (2) | 101 (3) | 105 (4) | 103 (6) | 107 (10) | 87 |
| | PQ | 0 | 0 | 0 | 0 | 0 | 0 | 0 |

[a]: The compounds are incubated at 37° C. in the presence of fetal calf serum (95% final) and then analyzed by spectrophotometry after HPLC. The initial purity of the compounds, determined by HPLC, is 99.5%, 98.6% and 99.5%, respectively.
[b]: The results represent the relative concentration of primaquine (PQ) and of derivatives (PQX) in terms of the incubation time, expressed as a percentage of the initial concentration (time 0) after extraction (mean +/− standard deviation; n = 4, PQ; n = 2, gGLU-PQ; and n = 4, pGLU-PQ).

obtain a 20% suspension of red cells ($2 \times 10^9$ erythrocytes/ml). To 1 ml of this suspension, 1 ml of a solution of PQ or derivatives at a concentration of 0.250 mM in the same medium at 37° C. is added.

After different incubation times at 37° C., 0.5 ml of sample is withdrawn and then transferred to an Eppendorf tube containing 0.4 ml of silicone oil (Merck, density 1.06 g/ml).

After centrifugation for 30 seconds at 12,000 g, the supernatant and the silicone oil are removed, while the cells in the pellet are lyzed by adding 0.5 ml of water. The quinoline compound present in combination with the cell lysate is then extracted by precipitation of the cell proteins with acetonitrile (0.5 ml) and thereafter analyzed by HPLC under the standard conditions.

The intracellular concentration of quinoline derivative is obtained by subtracting the concentration of compound present in the extracellular medium from the total concentration in the cell lysate. The contaminating extracellular volume is measured using tritiated inulin.

3.2. Results

PQ is taken up rapidly by erythrocytes (Table 3). After 5 minutes' incubation, 18% of the PQ present in the extracellular medium is to be found in the red cells, and this concentration is maintained for at least one hour.

gGLU-PQ is not accumulated in erythrocytes. pGLU-PQ accumulates more slowly than PQ; the maximum level is reached after 60 minutes and the concentration is similar to that of PQ.

TABLE 3

Permeability of human red cells to primaquine and amino acid derivatives

| COMPOUND [a] | CONCENTRATION [b] (% initial concentration) | | |
|---|---|---|---|
| | 5 min | 10 min | 60 min |
| Primaquine | 17.7 (1.2) | 18.0 (3.4) | 18.8 (0.2) |
| gGLU-PQ | 0 [c] | 0 | 0 |
| pGLU-PQ | 13.8 | 16.9 | 17.8 |

[a]: The compounds are incubated at a final concentration of 100 μg/ml in the presence of human red cells at a density of $10^9$ erythrocytes/ml.
[b]: The results represent the concentration of compounds combined with the erythrocytes and expressed as a percentage of the initial concentration (mean +/− standard deviation, n = 4 samples).
[c]: Compound not detectable under the analytical conditions used (detection threshold = 50 ng).

4. Hemolytic effect and methemoglobin production

Two important toxic effects of PQ were assessed on the two derivatives: the hemolytic effect and the conversion of hemoglobin to methemoglobin. The glutathione balance (reduced and oxidized form), which participates in the cell's defense mechanism against oxidizing agents, was also studied.

4.1. Protocol

A+ blood is washed twice in 0.15M phosphatebuffered saline at pH 7.4 containing 20 mM glucose (GPBS), and then resuspended at a concentration of 50% in the same buffer. To this suspension, an equal volume of compound dissolved in GPBS at different concentrations (test), or of GPBS (control) is added. The final hematocrit of the suspension is 25%. After 60 minutes' incubation at 37° C., the concentration of hemoglobin and methemoglobin is determined on the total suspension, and the concentration of hemoglobin present in the supernatant after centrifugation (extracellular hemoglobin) is determined, by the cyanmethemoglobin and benzidine methods (Fairbanks V.F., 1976, in "Fundamentals of Clinical Chemistry, M.W. Tietz Editors, Saunders"). The content of reduced glutathione (GSM) and oxidized glutathione (GSSG) is measured on the red cell suspension by the fluorimetric method of Hissin P.J. and Hilf R. (1976), Anal. Biochem., 74, 214–226).

4.2. Results

Table 4 shows the hemolysis, that is to say the concentration of extracellular hemoglobin after 60 minutes' incubation of erythrocytes in the presence of PQ and its derivatives.

PQ has a concentration-dependent hemolytic effect, 4.7% of the red cells being lyzed after 1 hour in the presence of 10 mM PQ. The hemolytic effect is also dependent on the incubation time (results not shown). The derivatives have a hemolytic activity comparable to that of PQ, representing, at a concentration of 5 mM, twice the hemolysis of the controls.

As regards methemoglobin production, the latter also depends on the concentration of aminoquinoline derivative In the case of PQ, 11.5% of hemoglobin are oxidized to methemoglobin when the erythrocytes are in the presence of 10 mM PQ for 1 hour (Table 4).

In the presence of the same concentration of derivative, the oxidation of hemoglobin is similar to that of PQ for gGLU-PQ and 1.5 times less for pGLU-PQ.

TABLE 4

Effect of primaquine and its amino acid derivatives on human red cells.

| COMPOUND [a] | CONCENTRATION (mM) | HEMOLYSIS [b] (%) | METHEMOGLOBIN [b] (%) |
|---|---|---|---|
| Primaquine | 0 (T 0) | 1.3 (0.6) | 1.3 (0.8) |
| | 0 (T 1) | 1.6 (0.4) | 1.4 (0.9) |
| | 1 | 2.1 (1.0) | 1.2 (0.5) |
| | 2 | 2.3 (1.1) | 3.4 (1.8) |
| | 5 | 2.8 (1.2) | 5.8 (0.2) |
| | 10 | 4.7 (1.7) | 11.5 (4.2) |
| gGLU-PQ | 0 (T 0) | 0.20 (0.1) | 1.2 (0.8) |
| | 0 (T 1) | 0.22 (0.05) | 1.0 (0.6) |
| | 1 | 0.27 (0.03) | 1.4 (0.0) |
| | 2 | — | — |
| | 5 | 0.58 (0.05) | 5.3 (0.0) |
| | 10 | — | — |
| pGLU-PQ | 0 (T 0) | 0.22 (0.02) | 1.2 (0.8) |
| | 0 (T 1) | 0.35 (0.03) | 1.0 (0.6) |
| | 1 | 0.32 (0.06) | 0.9 (0.1) |
| | 2 | 0.24 (0.02) | 2.2 (0.9) |
| | 5 | 0.44 (0.02) | 3.9 (0.0) |
| | 10 | 2.34 (0.06) | 6.0 (0.2) |

[a]: The compounds, at different concentrations, are incubated for 1 hour at 37° C. in the presence of human red cells (hematocrit 25%). Control without compound at time 0 (T 0) and after 1 hour's incubation (T 1).
[b]: The results represent the concentration of extracellular hemoglobin (hemolysis) and of methemoglobin (oxidized hemoglobin), expressed as a % of the total hemoglobin concentration in the respective sample (mean +/− standard deviation; n = 3 for PQ and n = 3 for gGLU-PQ and pGLU-PQ).

The concentration of reduced and oxidized glutathione after incubation of red cells with PQ and its derivatives is shown in Table 5.

EXAMPLE 3: EXPERIMENTAL TOXICITY IN ANIMALS

The acute toxicity in terms of a single administered dose is determined on female Swiss $OF_1$ mice weighing 22 to 25 g. A series of dilutions of each compound is injected intravenously into groups of 10 mice (0.1 ml per 10 g of weight).

The lethal dose for 50% of mice ($LD_{50}$) is determined by linear regression of the logits of the percentage of surviving animals as a function of the logarithm of the dose injected (in mg PQ diphosphate equivalent/kg). (Logit Weighted Transformation, Berkson J., 1953; J. Am. Stat. Assoc. 48, 565–599).

The results recorded in Table 6 show that the maximum tolerated dose (MTD), defined as the highest dose inducing a weight loss not exceeding 5% of the initial weight during a period of 5 days following i.v. injection, is 24 mg/kg for PQ, 117 mg/kg for gGlu-PQ and 126 mg/kg for pGLU-PQ.

The dose killing 50% of the animals (LD$_{50}$) after a single i.v. injection is 31 mg/kg for PQ, and 169 mg/kg and 159 mg/kg for the derivatives gGLU-PQ and pGLU-PQ, respectively.

TABLE 6

| | Comparative acute toxicity of primaquine and its derivatives in mice after a single i.v. administration. | |
| --- | --- | --- |
| PRODUCT [a] | MTD [b] (mg/kg) | LD$_{50}$ [c] (mg/kg) |
| Primaquine | 24 (2.1) | 31 (0.7) |
| gGLU-PQ | 117 (13) | 169 (9) |
| pGLU-PQ | 126 (13) | 159 (6) |

[a]: The products are administered i.v. to groups of 10 female Swiss OF$_1$ mice weighing 22 to 25 g, on the basis of 5 doses per product.
[b]: Maximum tolerated dose (MTD), defined as the highest dose inducing a weight loss not exceeding 5% of the initial weight during a period of 5 days following i.v. injection.
[c]: Lethal dose for 50% of the mice after a single i.v. administration.

EXAMPLE 4: ANTIMALARIAL ACTIVITY IN ANIMALS

1. Protocol

Primaquine and its derivatives are tested in the model of malaria in rodents employing the infection of mice with Plasmodium berghei, the sporozoites originating from infected Anopheles stephensi mosquitoes. This model, developed by Most H., Herman R. & Schoenfeld C. (1967), Am. J. Trop. med. Hyg. 16, 572–575, enables the casual prophylatic (tissue schizonticidal) activity of new therapeutic compounds to be determined.

The procedure used is that derived from Most H. & Montuori W.A. (1975), Am. J. Trop. Med. Hyg. 24, 179-189. It involves the system *P. berghei* (ANKA)-/*Anopheles stephensi*/Swiss OF$_1$ mice. The ANKA strain of *P. b. berghei* is maintained cyclically on *Anopheles stephensi*. The Swiss OF$_1$ strain mouse is especially sensitive to *P. b. berghei*, which produces an invariably fatal infection.

1.1. Isolation of sporozoites from mosquitoes and experimental infection

The legs, wings and abdomen are removed from female mosquitoes (80 to 100 individuals per preparation) and the latter are then homogenized at 4° C. in MEM medium (GIBCO) containing 10% of fetal calf serum using a glass Potter. The sporozoite suspension is then purified from the mosquito debris by two successive centrifugations (2 min at 50 g and 5 min at 200 g) and the collected supernatant is stored at 4° C. After counting in a Petroff-Hausser chamber, the number of parasites is adjusted by dilution with the same cold medium to a density of $2 \times 10^5$ sporozoites/ml.

The possible residual effect of the drugs on the primary erythrocytic forms (erythrocytic schizonticidal effect) is determined by the method of Gregory K.G. & Peters W. (An.. Trop. Med. Parasitol., 1970, 64, 15-24), based on Warhurst's 2% test.

The causal prophylactic activity of the compounds, that is to say the dose enabling 50% of the infected animals to be cured (CPD$_{50}$) is obtained by analysis of the logits of the response (expressed as a % LTS) as a function of the dose (mg PQ/kg).

The whole procedure is always performed in not more than 35 minutes, and enables the viability and infectivity of the sporozoites to be preserved.

A volume of 0.5 ml of the suspension containing $10^5$ sporozoites is injected i.v. into female Swiss OF$_1$ mice weighing 20 to 25 g, used for the therapeutic tests. 1.2. Chemotherapeutic treatments Groups of 20 to 25 mice, infected as described above, are treated with a single intravenous injection of primaquine diphosphate (PQ) or of its two derivatives in hydrochloride form, three hours after inoculation of the sporozoites. The volume injected is adjusted according to the weight of the mouse, on the basis of 0.25 ml for a weight of 25 g. The compounds are diluted in phosphatebuffered saline (PBS), pH 7.0, and the pH is adjusted to 7.0. Infected but untreated mice (5 per group), receive the buffer alone and serve to monitor the infectivity of the sporozoites.

1.3. Parameters used for evaluating the efficacy of primaquine and its derivatives The experimental mice are kept for a period of 50 days. The development of the parasitemia is followed by daily examination of blood smears stained for 60 min with 5% Giemsa in Sorensen buffer at pH 7.2, from day 5 up to day 15. The number of infected animals can thus be determined. These results enable the long-term survival (LTS, the number of non-parasitized surviving mice over the number of infected and treated mice) to be established.

2. Therapeutic activity in animals

The animals infected using P. berchei sporozoites are treated three hours later with a single i.v. injection of the compounds. This test enables the casual prophylactic activity of the compounds, that is the dose enabling 50% of the infected animals to be cured (CPD$_{50}$), to be defined. The dose is always expressed as mg of PQ diphosphate per kg.

The results for the causal prophylactic activity (+ three hours) of primaquine and its two amino acid derivatives are shown in Table 7. They indicate clearly that the two derivatives are more active than PQ, the dose inducing cure in 50% of the animals (CPD$_{50}$) being 22-fold lower for gGLU-PQ and 1.9-fold for pGLU-PQ than for PQ.

The minimal effective dose of the two derivatives is also lower than that of PQ. While the totally curative dose cannot be reached in a single injection for PQ on account of its toxicity (ED$_{100}$ of PQ estimated at 54 mg/kg), those of gGLU-PQ and pGLU-PQ are reached at 24 mg/kg and 22 mg/kg, respectively.

TABLE 7

| Causal prophylactic activity of primaquine and its amino acid derivatives on OF$_1$ mice infected with *Plasmodium berghei*. | | | | |
| --- | --- | --- | --- | --- |
| COMPOUND [a] | CPD$_{50}$ [b] (mg/kg) | MED [c] (mg/kg) | ED$_{100}$ [c] (mg/kg) | PQ INDEX [d] |
| Primaquine | 18.8 (1.3) | 6.5 (2.6) | TOX | 1.00 |
| gGLU-PQ | 8.7 (0.7) | 3.2 (1.1) | 24.2 (9.8) | 2.15 |
| pGLU-PQ | 10.0 (0.7) | 4.6 (1.3) | 21.8 (5.7) | 1.87 |

[a]: The compounds are administered i.v. three hours after inoculation of the sporozoites. The concentrations are expressed as mg PQ diphosphate equivalent/kg.
[b]: Causal prophylactic dose curing 50% of the infected and treated animals.
[c]: Minimal effective dose (MED) and totally curative dose (ED$_{100}$) calculated by linear regression (Weighted Logit Transformation).
[d]: PQ index = ratio CPD$_{50}$ of PQ/CPD$_{50}$ of the compound.

3. Therapeutic index

The therapeutic index is defined as the ratio of the toxicity, expressed as LD$_{50}$, to the therapeutic activity, expressed as CPD$_{50}$, in mice.

The therapeutic index of PQ is 1.7 (Table 8), while it is above 15 and 19 for pGLU-PQ and gGLU-PQ.

The experimental data on activity in the model of malaria in mice and the toxicity data indicate that gGLU-PQ has a therapeutic index at least 11-fold higher than that of PQ, the derivative being at least 5-fold less toxic than and at least twice as active as PQ in this experimental model of malaria.

The same applies to the derivative pGLU-PQ with a therapeutic index 9-fold greater than that of PQ, the derivative being at least 5-fold less toxic than and at least 1.9-fold as active as PQ.

TABLE 8

| Therapeutic index of primaquine and amino acid derivatives | | | |
|---|---|---|---|
| PRODUCTS [a] | LD$_{50}$ (mg/kg) | CPD$_{50}$ (mg/kg) | TI [b] |
| PQ | 31 (0.7) | 18.8 (1.3) | 1.7 |
| gGLU-PQ | 169 (9) | 8.7 (0.7) | 19.4 |
| pGLU-PQ | 159 (6) | 10.0 (0.7) | 15.9 |

[a]: The products are inoculated i.v. and the concentrations are expressed as PQ diphosphate equivalents.
[b]: The therapeutic index (TI) is the ratio of LD$_{50}$ to CPD$_{50}$.

EXAMPLE 5: L-ASPARTYL PRIMAQUINE DERIVATIVE

1. Synthesis

The aspartic acid derivatives of primaquine are obtained by the condensation of primaquine with an activated ester of aspartic acid according to the same method of synthesis described for the glutamic acid derivatives of primaquine.

The L-aspartic acid derivative of primaquine (ASP-PQ) is synthesized according to the procedure used for the gamma-glutamic acid derivative of primaquine, but protecting the beta -carboxyl group instead of the alphacarboxyl group. The beta -L-aspartic acid derivative of primaquine ($\beta$ASP-PQ) is obtained according to the procedure used for gGLU-PQ.

The compounds are obtained in the form of a base (M.W. 374.43) and of a dihydrochloride salt (M.W. 447.35).

2. Experimental toxicity in animals

The acute toxicity in terms of a single administered dose is determined under the same conditions and according the protocol of Example 3.

The results recorded in Table 9 show that the maximum tolerated dose (MTD), defined as the highest dose inducing a weight loss not exceeding 5% of the initial weight during a period of 5 days following i.v. injection, is 24 mg/kg for PQ, 107 mg/kg for ASP-PQ and 109 mg/kg for gASP-PQ.

The dose killing 50% of the animals (LD$_{50}$) after a single i.v. injection is 31 mg/kg for PQ, and 165 mg/kg and 164 mg/kg for the derivatives ASP-PQ and $\beta$ASP-PQ, respectively.

TABLE 9

| Comparative acute toxicity of primaquine and its derivatives in mice after a single i.v. administration. | | |
|---|---|---|
| PRODUCT [a] | MTD [b] (mg/kg) | LD$_{50}$ [c] (mg/kg) |
| Primaquine | 24 (2.1) | 31 (0.7) |
| ASP-PQ | 107.2 (14.2) | 165.5 (5.4) |
| $\beta$ASP-PQ | 109.1 (13.1) | 164.4 (6.2) |

[a]: The products are administered i.v. to groups of 10 female Swiss OF$_1$ mice weighing 22 to 25 g. on the basis of 5 doses per product.
[b]: Maximum tolerated dose (MTD), defined as the highest dose inducing a weight loss not exceeding 5% of the initial weight during a period of 5 days following i.v. injection.
[c]: Lethal dose for 50% of the mice after a single i.v. administration.

3. Therapeutic activity in animals

The animals infected using P. berghei sporozoites are treated three hours later with a single i.v. injection of the compounds. This test enables the casual prophylactic activity of the compounds, that is the dose enabling 50% of the infected animals to be cured (CPD$_{50}$), to be defined. The dose is always expressed as mg of PQ diphosphate per kg.

The results for the casual prophylactic activity (+ three hours) of primaquine and its amino acid derivatives are shown in Table 10. They indicate clearly that the two derivatives are more active than PQ, the dose inducing cure in 50% of the animals (CPD$_{50}$) being 1.6-fold lower for ASP-PQ and $\beta$ASP-PQ than for PQ.

The minimal effective dose of the two derivatives is also lower than that of PQ. While the totally curative dose cannot be reached in a single injection for PQ on account of its toxicity (ED$_{100}$ of PQ estimated at 54 mg/kg), those of ASP-PQ and of $\beta$ASP-PQ are reached at 31 mg/kg.

TABLE 10

| Causal prophylactic activity of primaquine and its amino acid derivatives on OF$_1$ mice infected with Plasmodium berghei. | | | | |
|---|---|---|---|---|
| COMPOUND [a] | CPD$_{50}$ [b] (mg/kg) | MED [c] (mg/kg) | ED$_{100}$ [c] (mg/kg) | PQ INDEX [d] |
| Primaquine | 18.8 (1.3) | 6.5 (2.6) | TOX | 1.00 |
| ASP-PQ | 11.6 (0.9) | 4.4 (1.3) | 31.1 (9.2) | 1.62 |
| $\beta$ASP-PQ | 11.2 (0.7) | 4.1 (1.1) | 30.6 (5.7) | 1.68 |

[a]: The compounds are administered i.v. three hours after inoculation of the sporozoites. The concentrations are expressed as mg PQ diphosphate equivalent/kg.
[b]: Causal prophylactic dose curing 50% of the infected and treated animals.
[c]: Minimal effective dose (MED) and totally curative dose (ED$_{100}$) calculated by linear regression (Weighted Logit Transformation).
[d]: PQ index = ratio CPD$_{50}$ of PQ/CPD$_{50}$ of the compound.

4. Therapeutic index

The therapeutic index is defined as the ratio of the toxicity, expressed as LD$_{50}$, to the therapeutic activity, expressed as CPD$_{50}$, in mice.

The therapeutic index of PQ is 1.7 (Table 11), while it is above 14 for both ASP-PQ and $\beta$ASP-PQ.

The experimental data on activity in the model of malaria in mice and the toxicity data indicate that ASP-PQ has a therapeutic index at least 8-fold higher than that of PQ, the derivative being at least 5-fold less toxic than and 1.6-fold as active as PQ in this experimental model of malaria.

The same applies to the derivative $\beta$ASP-PQ with a therapeutic index 8-fold greater than that of PQ, the derivative being at least 5-fold less toxic than and at least 1.6-fold as active as PQ.

TABLE 11

| Therapeutic index of primaquine and amino acid derivatives | | | |
|---|---|---|---|
| PRODUCT [a] | LD$_{50}$ (mg/kg) | CPD$_{50}$ (mg/kg) | TI [b] |
| Primaquine | 31 (0.7) | 18.8 (1.3) | 1.7 |
| ASP-PQ | 165 (5.4) | 11.6 (0.9) | 14.3 |
| $\beta$ASP-PQ | 164 (6.2) | 11.2 (0.7) | 14.7 |

[a]: The products are inoculated i.v. and the concentrations are expressed as PQ diphosphate equivalents.
[b]: The therapeutic index (TI) is the ratio of processed LD$_{50}$ value to the processed CPD$_{50}$ value.

We claim:

1. A quinoline derivative containing a free amine group and having antimalarial properties, or its addition salts with acids, wherein the quinoline derivative is represented schematically by the formula:

PQ-X in which

PQ denotes quinolines containing a free amine group and having antimalarial properties, and X is selected from the group consisting of gamma-L-glutamic acid, L-pyroglutamic acid and beta-L-aspartic acid, wherein the PQ-X bond is a convalent peptide bond between the free amine group of PQ and a carboxyl group of the selected amino acid and wherein further the bond is stable in serum and resistant to lysosomal hydrolases.

2. The quinoline derivatives of claim 1, wherein the quinolines denoted by PQ are 8-aminoquinolines.

3. The quinoline derivatives of claim 1, wherein the quinolines denoted by PQ is primaquine.

4. A pharmaceutical composition, comprising, as an active principle, quinoline derivatives selected from the group consisting of the derivatives as claimed in claim 1 and their pharmaceutically acceptable salts.

* * * * *